(12) United States Patent
Herold et al.

(10) Patent No.: US 8,324,235 B2
(45) Date of Patent: Dec. 4, 2012

(54) HETEROCYCLIC SPIRO-COMPOUNDS

(75) Inventors: Peter Herold, Münchenstein (CH); Robert Mah, Muttenz (CH); Stefan Stutz, Basel (CH); Vincenzo Tschinke, Binningen (CH); Aleksandar Stojanovic, Basel (CH); Nathalie Jotterand, Basel (CH); Bibia Bennacer, Altkirch (FR)

(73) Assignee: Novartis AG, Basel (CH)

( * ) Notice: Subject to any disclaimer, the term of this patent is extended or adjusted under 35 U.S.C. 154(b) by 394 days.

(21) Appl. No.: 12/450,521

(22) PCT Filed: Mar. 27, 2008

(86) PCT No.: PCT/EP2008/053671
§ 371 (c)(1),
(2), (4) Date: Feb. 3, 2010

(87) PCT Pub. No.: WO2008/119744
PCT Pub. Date: Oct. 9, 2008

(65) Prior Publication Data
US 2010/0144774 A1  Jun. 10, 2010

(30) Foreign Application Priority Data

Mar. 29, 2007 (EP) .................................... 07105246

(51) Int. Cl.
*A61K 31/4188* (2006.01)
*C07D 401/14* (2006.01)
*C07D 235/02* (2006.01)
(52) U.S. Cl. ........ 514/278; 514/409; 546/18; 548/301.1
(58) Field of Classification Search .................... 546/18; 548/301.1
See application file for complete search history.

(56) References Cited

FOREIGN PATENT DOCUMENTS

| | | |
|---|---|---|
| WO | 2006/128852 | 12/2006 |
| WO | 2006/128853 | 12/2006 |

OTHER PUBLICATIONS

Pulmonary fibrosis [online] retrieved on Feb. 11, 2012 from the internet (URL; http://www.mayoclinic.com/health/pulmonary-fibrosis/DS00927).*
Fibrosis—What is Fibrosis? [online} retrieved from the internet on Feb. 11, 2012 (URL; http://www.news-medical.net/health/Fibrosis-What-is-Fibrosis.aspx.*
International Search Report issued Aug. 4, 2008 in International (PCT) Application No. PCT/EP2008/053671.
Written Opinion issued Aug. 4, 2008 in International (PCT) Application No. PCT/EP2008/053671.

* cited by examiner

*Primary Examiner* — Shawquia Young
(74) *Attorney, Agent, or Firm* — Wenderoth, Lind & Ponack, L.L.P.

(57) ABSTRACT

The patent application relates to new heterocyclic compounds of the general formula (I), in which R, $R^1$, $R^2$, Q, T, n and p have the definitions elucidated in more detail in the description, to a process for preparing them and to the use of these compounds as medicaments, particularly as aldosterone synthase inhibitors.

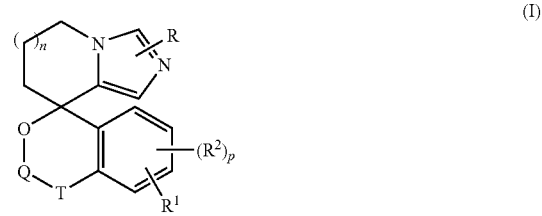

13 Claims, No Drawings

HETEROCYCLIC SPIRO-COMPOUNDS

FIELD OF THE INVENTION

The invention relates to new heterocycles, to processes for preparing the compounds according to the invention, to pharmaceutical products comprising them, and to their use as active pharmaceutical ingredients, in particular as aldosterone synthase inhibitors.

BACKGROUND OF THE INVENTION

WO2006/128852 and WO2006/128853 describe heterocyclic spiro compounds as medicines for hormone-dependent diseases, particularly for the treatment of hyperaldosteronism. However, the development of imidazole derivatives as new medicines for conditions of absolute or relative aldosterone excess by inhibition of the enzyme aldosterone synthase or cytochrome P450 11B2 (CYP11B2), requires derivatives with improved target efficacy and selectivity as well as pharmacological properties. As such, target efficacy is enhanced with better dose-dependent CYP11B2 inhibitory properties in vitro and in vivo. Target selectivity and hence drug tolerability and safety is improved with reduced interference with related cytochrom P450 enzymes such as 11beta hydroxylase and aromatase. The pharmacological properties are ameliorated with better drug bioavailability, tissue distribution and duration of action as determined by increased absorption, metabolic stability or solubility, or optimized lipophilicity and elimination kinetics.

DETAILED DESCRIPTION OF THE INVENTION

The present invention provides compounds of the general formula (I)

in which
Q is —C($R^3$)($R^4$)— or a bond;
T is —C($R^3$)($R^4$)—;
R is hydrogen or deuterium;
$R^1$ is $C_1$-$C_8$-alkyl, $C_0$-$C_8$-alkylcarbonyl, amino, mono- or di-$C_1$-$C_8$-alkylamino, $C_0$-$C_8$-alkylcarbonylamino, $C_0$-$C_8$-alkylcarbonyl-$C_1$-$C_8$-alkylamino, carbamoyl, mono- or di-$C_1$-$C_8$-alkylaminocarbonyl, carboxyl, carboxy-$C_1$-$C_4$-alkyl, halogen, cyano, methylsulfonyl, nitro, trifluoromethyl, $C_1$-$C_8$-alkoxy, $C_1$-$C_8$-alkoxycarbonyl, heterocyclyl or aryl, which radicals may be unsubstituted or substituted by 1-4 $C_1$-$C_8$-alkyl, $C_0$-$C_8$-alkylcarbonyl, halogen, cyano, oxo, trifluoromethyl, trifluoromethoxy, $C_0$-$C_8$-alkylcarbonylamino, $C_0$-$C_8$-alkylcarbonyl-$C_1$-$C_8$-alkylamino, carbamoyl, mono- and di-$C_1$-$C_8$-alkylaminocarbonyl, carboxy-$C_0$-$C_4$-alkyl, $C_1$-$C_8$-alkoxy, $C_1$-$C_8$-alkoxycarbonyl, aryl or heterocyclyl;
$R^2$ is, if p is not 0, independently of one another, $C_1$-$C_8$-alkyl, $C_0$-$C_8$-alkylcarbonyl, amino, mono- and di-$C_1$-$C_8$-alkylamino, $C_0$-$C_8$-alkylcarbonylamino, $C_0$-$C_8$-alkylcarbonyl-$C_1$-$C_8$-alkylamino, carbamoyl, mono- or di-$C_1$-$C_8$-alkylaminocarbonyl, carboxyl, carboxy-$C_1$-$C_4$-alkyl, halogen, cyano, methylsulfonyl, nitro, trifluoromethyl, trifluoromethoxy, $C_1$-$C_8$-alkoxy, $C_1$-$C_8$-alkoxycarbonyl, heterocyclyl or aryl, which radicals may be unsubstituted or substituted by 1-4 $C_1$-$C_8$-alkyl, $C_0$-$C_8$-alkylcarbonyl, halogen, cyano, oxo, trifluoromethyl, trifluoromethoxy, $C_0$-$C_8$-alkylcarbonylamino, $C_0$-$C_8$-alkylcarbonyl-$C_1$-$C_8$-alkylamino, carbamoyl, mono- and di-$C_1$-$C_8$-alkylaminocarbonyl, carboxy-$C_0$-$C_4$-alkyl, $C_1$-$C_8$-alkoxy, $C_1$-$C_8$-alkoxycarbonyl, aryl or heterocyclyl;
$R^3$ is, independently of one another:
  a) hydrogen or $C_1$-$C_8$-alkyl; or
  b) together with $R^4$ oxo;
$R^4$ is, independently of one another:
  a) hydrogen or $C_1$-$C_8$-alkyl; or
  b) together with $R^3$ oxo;
n is a number 0, 1 or 2;
p is a number 0, 1 or 2;
and their salts, preferably their pharmaceutically useful salts.

The aryl term stands for an aromatic hydrocarbon which contains generally 5-14, preferably 6-10, carbon atoms and is for example phenyl, or naphthyl, e.g. 1- or 2-naphthyl. Preference is given to aryl having 6-10 carbon atoms, particularly phenyl or 1- or 2-naphthyl. The stated radicals may be unsubstituted or may be substituted one or more times, such as once or twice, in which case the substituent may be in any position, such as in the o, m or p position of the phenyl radical or in the 3 or 4 position of the 1- or 2-naphthyl radical, and there may also be two or more identical or different substituents.

The heterocyclyl term stands for a saturated or unsaturated, 4-8-membered, more preferably 5-membered, monocyclic ring system, for a saturated or unsaturated, 7-12-membered, more preferably 9-10-membered, bicyclic ring system, and alternatively for a saturated or unsaturated 7-12-membered tricyclic ring system, in each case containing an N, O or S atom in at least one ring, it also being possible for an additional N, O or S atom to be present in one ring, and the heteroatoms being separated preferably by at least one C atom. The stated radicals may be unsubstituted or may be substituted one or more times, such as once or twice, and there may also be two or more identical or different substituents.

Unsaturated monocyclic heterocyclyl-$C_0$-$C_4$-alkyl is for example furyl, pyrrolyl, thiophenyl, thiazolyl or oxazolyl.

Saturated monocyclic heterocyclyl-$C_0$-$C_4$-alkyl is for example pyrrolidinyl.

Unsaturated bicyclic heterocyclyl-$C_0$-$C_4$-alkyl is for example 4,5,6,7-tetrahydroisobenzofuranyl, 4,5,6,7-tetrahydrobenzothiazolyl, benzofuranyl, benzothiophenyl, isoquinolyl or quinolyl.

$C_1$-$C_8$-Alkyl can be linear or branched and/or bridged and is for example methyl, ethyl, propyl, isopropyl, butyl, isobutyl, secondary-butyl, tertiary-butyl, or a pentyl, hexyl or heptyl group.

$C_1$-$C_8$-Alkoxy is for example $C_1$-$C_5$-alkoxy, such as methoxy, ethoxy, propyloxy, isopropyloxy, butyloxy, isobutyloxy, secondary-butyloxy, tertiary-butyloxy or pentyloxy, but can also be a hexyloxy or heptyloxy group.

$C_1$-$C_8$-Alkoxycarbonyl is preferably $C_1$-$C_4$-alkoxycarbonyl, such as methoxycarbonyl, ethoxycarbonyl, propyloxycarbonyl, isopropyloxycarbonyl, butyloxycarbonyl, isobutyloxycarbonyl, secondary-butyloxycarbonyl or tertiary-butyloxycarbonyl.

$C_0$-$C_8$-Alkylcarbonyl is for example formyl, acetyl, propionyl, propylcarbonyl, isopropylcarbonyl, butylcarbonyl, isobutylcarbonyl, secondary-butylcarbonyl or tertiary-butylcarbonyl.

Halogen is for example fluoro, chloro, bromo or iodo.

Carboxy-$C_1$-$C_4$-alkyl is for example carboxymethyl, 2-carboxyethyl, 2- or 3-carboxypropyl, 2-carboxy-2-methylpropyl, 2-carboxy-2-ethylbutyl or 4-carboxybutyl, especially carboxymethyl.

Mono- or di-$C_1$-$C_8$-alkylamino is for example $C_1$-$C_4$-alkylamino, such as methylamino, ethylamino, propylamino or butylamino, or di-$C_1$-$C_4$-alkylamino, such as dimethylamino, N-methyl-N-ethylamino, diethylamino, N-methyl-N-propylamino or N-butyl-N-methylamino.

Mono- or di-$C_1$-$C_8$-alkylaminocarbonyl is for example $C_1$-$C_4$-alkylaminocarbonyl, such as methylaminocarbonyl, ethylaminocarbonyl, propylaminocarbonyl or butylaminocarbonyl, or di-$C_1$-$C_4$-alkylaminocarbonyl, such as dimethylaminocarbonyl, N-methyl-N-ethylaminocarbonyl, diethylaminocarbonyl, N-methyl-N-propylaminocarbonyl or N-butyl-N-methylaminocarbonyl.

$C_0$-$C_8$-Alkylcarbonylamino is for example formylamino, acetylamino, propionylamino, propylcarbonylamino, isopropylcarbonylamino, butylcarbonylamino, isobutylcarbonylamino, secondary-butylcarbonylamino or tertiary-butylcarbonylamino.

$C_0$-$C_8$-Alkylcarbonyl-$C_1$-$C_8$-alkylamino is for example formyl-, acetyl-, propionyl-, propylcarbonyl-, isopropylcarbonyl-, butylcarbonyl-, isobutylcarbonyl-, secondary-butylcarbonyl- or tertiary-butylcarbonyl-methylamino, formyl-, acetyl-, propionyl-, propylcarbonyl-, isopropylcarbonyl-, butylcarbonyl-, isobutylcarbonyl-, secondary-butylcarbonyl- or tertiary-butylcarbonyl-ethylamino, formyl-, acetyl-, propionyl-, propylcarbonyl-, isopropylcarbonyl-, butylcarbonyl-, isobutylcarbonyl-, secondary-butylcarbonyl- or tertiary-butylcarbonyl-propylamino or formyl-, acetyl-, propionyl-, propylcarbonyl-, isopropylcarbonyl-, butylcarbonyl-, isobutylcarbonyl-, secondary-butylcarbonyl- or tertiary-butylcarbonyl-butylamino.

The groups of compounds specified below should not be considered as being closed; on the contrary, parts of these groups of compounds may be replaced by one another or by the definitions given above, or may be omitted, in a meaningful way, such as in order to replace more general definitions by more specific definitions.

$R^1$ is preferably $C_1$-$C_8$-alkyl, $C_0$-$C_8$-alkylcarbonyl, halogen, cyano, methylsulfonyl, nitro, trifluoromethyl, trifluoromethoxy, $C_0$-$C_8$-alkylcarbonylamino, $C_0$-$C_8$-alkylcarbonyl-$C_1$-$C_8$-alkylamino, carbamoyl, mono- and di-$C_1$-$C_8$-alkylaminocarbonyl, carboxy-$C_0$-$C_4$-alkyl, $C_1$-$C_8$-alkoxy, $C_1$-$C_8$-alkoxycarbonyl or heterocyclyl, very preferably acetyl, halogen, cyano, methylsulfonyl or nitro and most preferably cyano or halogen, the most preferred halogen is fluoro.

$R^2$ is preferably, if p is not 0, independently of one another, halogen, cyano, methylsulfonyl, nitro, trifluoromethyl, trifluoromethoxy, or $C_1$-$C_8$-alkyl, very preferably halogen, cyano, methylsulfonyl, nitro or $C_1$-$C_8$-alkyl and most preferably cyano or halogen.

n is preferably a number 0 or 1.

p is preferably a number 0 or 1.

Preferred compounds of the formula (I) are those, wherein $R^1$ is $C_1$-$C_8$-alkyl, $C_0$-$C_8$-alkylcarbonyl, halogen, cyano, methylsulfonyl, nitro, trifluoromethyl, trifluoromethoxy, $C_0$-$C_8$-alkylcarbonylamino, $C_0$-$C_8$-alkylcarbonyl-$C_1$-$C_8$-alkylamino, carbamoyl, mono- and di-$C_1$-$C_8$-alkylaminocarbonyl, carboxy-$C_0$-$C_4$-alkyl, $C_1$-$C_8$-alkoxy, $C_1$-$C_8$-alkoxycarbonyl or heterocyclyl, preferably acetyl, halogen, cyano, methylsulfonyl or nitro, most preferably cyano or halogen, the most preferred halogen is fluoro;

$R^2$ is, if p is not 0, independently of one another, halogen, cyano, methylsulfonyl, nitro, trifluoromethyl, trifluoromethoxy, or $C_1$-$C_8$-alkyl, preferably halogen, cyano, methylsulfonyl, nitro or $C_1$-$C_8$-alkyl, most preferably cyano or halogen;

n is a number 0 or 1; and p is a number 0 or 1.

Preferred substituents for aryl or heterocyclyl are halogen, cyano, trifluoromethyl, heterocyclyl or $C_1$-$C_8$-alkylcarbonyl. Very preferred substituents for aryl or heterocyclyl are halogen, cyano, thiophenyl, thiazolyl, oxazolyl or acetyl.

Very particular preference is therefore given, for example, to compounds of the general formula (I) in which $R^1$ is acetyl, halogen, cyano, methylsulfonyl or nitro; and $R^2$ is, if p is not 0, independently of one another, hydrogen, halogen, cyano, methylsulfonyl, nitro or $C_1$-$C_8$-alkyl.

Particularly preferred compounds of the formula (I) are those of the general formula (I') having a specific configuration at the asymmetric carbon atom labelled "*":

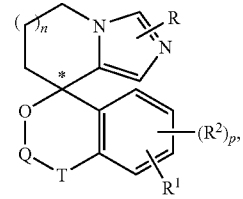

(I')

the definitions and preferences of the substituents R, $R^1$, $R^2$, Q, T, n and p being as specified for the compounds of the formula (I).

The compounds of the formula (I) which possess at least one asymmetric carbon atom can exist in the form of optically pure enantiomers, mixtures of enantiomers, or racemates. Compounds having a second asymmetric carbon atom can exist in the form of optically pure diastereomers, mixtures of diastereomers, diastereomeric racemates, mixtures of diastereomeric racemates, or mesocompounds. The invention embraces all of these forms. Mixtures of enantiomers, racemates, mixtures of diastereomers, diastereomeric racemates, or mixtures of diastereomeric racemates can be fractionated by conventional methods, such as by racemate resolution, column chromatography, thin-layer chromatography, HPLC and the like.

The compounds of the formula (I') have at least one asymmetric carbon atom, which is labelled "*". A compound of the formula (I') is to be understood as a compound having a specific configuration around the designated asymmetric carbon atom. If a synthesis method is used which leads to racemic compounds, the racemate resolution is carried out in accordance with conventional methods, such as via a chiral HPLC column. Compounds of the formula (I') as described in the present invention exhibit a pronounced aldosterone synthase and/or 11-β-hydroxylase inhibitory activity and a low aromatase inhibitory activity. The aforementioned aromatase inhibitory activity can, as the skilled worker is well aware and as described below, be comfortably determined via the commercial Cyp19 enzyme inhibition kit (vide infra). In the abovementioned inhibition kit, compounds of the formula (I') have an activity which is at least 10 times lower, preferably 20 times lower than the compounds of the formula (I') with the opposite configuration around the asymmetric carbon atom labelled "*".

Example of enantiomers with differing aromatase inhibition:

| Compound of Example | IC$_{50}$ value [nM]* |
|---|---|
| 23 | 922.2 |
| antipode of 23 | 31.8 |

*A lower inhibiting activity corresponds to a higher IC$_{50}$ value

The expression "pharmaceutically useful salts" embraces salts with organic or inorganic acids, such as hydrochloric acid, hydrobromic acid, nitric acid, sulfuric acid, phosphoric acid, citric acid, formic acid, maleic acid, acetic acid, succinic acid, tartaric acid, methanesulfonic acid, p-toluenesulfonic acid and the like. Salts of compounds containing salt-forming groups are, in particular, acid addition salts, salts with bases or else, if appropriate, if two or more salt-forming groups are present, are mixed salts or inner salts.

The compounds of the formula (I) can be prepared analogously to preparation processes known from the literature. Details of the specific preparation variants can be found from the examples.

The compounds of the formula (I) can also be prepared in optically pure form. Separation into antipodes is possible by methods known per se, either, preferably, at an early stage in synthesis, by salt formation with an optically active acid such as, for example, (+)- or (−)-mandelic acid and separation of the diastereomeric salts by fractional crystallization, or, preferably, at a fairly late stage, by derivatization with a chiral auxiliary component, such as, for example, (+)- or (−)-camphanyl chloride and separation of the diastereomeric products by chromatography and/or crystallization and subsequent cleavage of the bond to the chiral auxiliary. The pure diastereomeric salts and derivatives can be analysed to determine the absolute configuration of the compound present, using customary spectroscopic methods, with single-crystal X-ray spectroscopy representing one particularly appropriate method.

Salts are primarily the pharmaceutically useful or non-toxic salts of compounds of the formula (I). Such salts are formed for example by compounds of the formula (I) containing an acidic group, such as a carboxyl or sulfo group and are, for example, salts thereof with suitable bases, such as non-toxic metal salts derived from metals of group Ia, Ib, IIa and IIb of the Periodic Table of the Elements, such as alkali metal salts, especially lithium, sodium or potassium salts, alkaline earth metal salts, magnesium or calcium salts for example, and also zinc salts or ammonium salts, and additionally salts formed with organic amines, such as unsubstituted or hydroxyl-substituted mono-, di- or trialkylamines, especially mono-, di- or tri-lower alkylamines, or with quaternary ammonium bases, e.g. methyl-, ethyl-, diethyl- or triethylamine, mono-, bis- or tris(2-hydroxy-lower alkyl) amines, such as ethanolamine, diethanol-amine or triethanolamine, tris(hydroxymethyl)methylamine or 2-hydroxy-tertiary-butylamine, N,N-di-lower alkyl-N-(hydroxy-lower alkyl)amine, such as N,N-di-N-dimethyl-N-(2-hydroxyethyl)amine, or N-methyl-D-glucamine, or quaternary ammonium hydroxides, such as tetrabutylammonium hydroxide. The compounds of the formula (I) containing a basic group, such as amino group, can form acid addition salts, with suitable inorganic acids for example, such as hydrohalic acid, such as hydrochloric acid, hydrobromic acid, or sulfuric acid with replacement of one or both protons, phosphoric acid with replacement of one or more protons, orthophosphoric acid or metaphosphoric acid for example, or pyrophosphoric acid with replacement of one or more protons, or with organic carboxylic, sulfonic or phosphonic acids or N-substituted sulfamic acids, examples being acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxy-benzoic acid, 2-acetoxybenzoic acid, embonic acid, nicotinic acid, isonicotinic acid, and also amino acids, such as α-amino acids, and also methanesulfonic acid, ethanesulfonic acid, 2-hydroxyethanesulfonic acid, ethane-1,2-disulfonic acid, benzenesulfonic acid, 4-toluenesulfonic acid, naphthalene-2-sulfonic acid, 2- or 3-phosphoglycerate, glucose 6-phosphate, N-cyclohexylsulfamic acid (to form cyclamates), or with other acidic organic compounds, such as ascorbic acid. Compounds of the formula (I) containing acidic and basic groups can also form inner salts.

Isolation and purification can also be carried out using pharmaceutically unsuitable salts.

The compounds of the formula (I) also include those compounds in which one or more atoms have been replaced by their stable, non-radioactive isotopes: for example, a hydrogen atom by deuterium.

Prodrug derivatives of the presently described compounds are derivatives thereof which when employed in vivo release the original compound as a result of a chemical or physiological process. A prodrug may be converted into the original compound, for example, when a physiological pH is reached or as a result of enzymatic conversion. Examples of possible prodrug derivatives include esters of freely available carboxylic acids, S- and O-acyl derivatives of thiols, alcohols or phenols, the acyl group being defined as above. Preference is given to pharmaceutically useful ester derivatives which are converted by solvolysis in physiological medium into the original carboxylic acid, such as, for example, lower alkyl esters, cycloalkyl esters, lower alkenyl esters, benzyl esters, mono- or disubstituted lower alkyl esters, such as lower ω-(amino, mono- or dialkylamino, carboxyl, lower alkoxycarbonyl)-alkyl esters or such as lower α-(alkanoyloxy, alkoxycarbonyl or dialkylaminocarbonyl)alkyl esters; pivaloyloxymethyl esters and similar esters are conventionally used as ester derivatives of this kind.

Because of the close relationship between a free compound, a prodrug derivative and a salt compound, a defined compound in this invention also includes its prodrug derivative and salt form, insofar as this is possible and appropriate.

Aldosterone is a steroidal hormone which is synthesized in the zona glomerulosa of the adrenal gland by the cytochrom P450 enzyme aldosterone synthase (CYP11B2) in human as well as in rodent species. Aldosterone production and secretion is regulated by the adrenocorticotropic hormone (ACTH), angiotensin II, potassium and sodium ions. The primary biological function of aldosterone is the regulation of the salt balance, with aldosterone controlling the reabsorption of sodium ions from the renal filtrate and the secretion of potassium ions into the renal filtrate. Additional functions include the regulation of tissue homeostasis and inflammatory responses. The state of excessive aldosterone secretion, also called hyperaldosteronism, can lead to high blood pressure, hypokalemia, metabolic alkalosis, muscle weakness, polyuria, polydipsia, oedemas, vasculitis, increased collagen formation, fibrosis and endothelial dysfunction.

One aspect of the present invention pertains to the compounds of formula (I) or (I') or a pharmaceutically useful salt thereof for use in a method of treatment (e.g., of a disease condition) of the human or animal body by therapy.

One aspect of the present invention pertains to the use of the compounds of formula (I) or (I') or a pharmaceutically useful salt thereof for the manufacture of a medicament for use in the treatment of a disease condition.

One aspect of the present invention pertains to the use of the compounds of formula (I) or (I') or a pharmaceutically useful salt thereof in the treatment of a disease condition.

One aspect of the present invention pertains to a method of treatment of a disease condition in a patient, comprising administering to said patient a therapeutically-effective amount of a compound of formula (I) or (I') or a pharmaceutically useful salt thereof.

Disease Conditions

The chemical compounds described in this invention inhibit aldosterone synthase (CYP11B2) and can therefore be used to suppress aldosterone production and thus aldosterone-mediated disease conditions, such as hypokalemia, essential hypertension, secondary hypertension, congestive heart failure, acute and—in particular—chronic renal failure, cardiovascular restenosis, inflammation, atherosclerosis, metabolic syndrome (syndrome X), adiposity (obesity), vasculitis, vascular compliance, thrombosis, primary and secondary hyperaldosteronism, nephrosclerosis, nephropathy, retinopathy, myocardial infarction, cardiac arrhythmias, stroke, coronary heart disease, inappropriate sympathetic or parasympathetic nervous outflow, increased collagen formation, fibrosis, ascites, cirrhosis, sleep apnoe, vascular and coronary tissue changes (remodelling) secondary to high blood pressure, endothelial dysfunction, and oedemas secondary to cirrhosis, nephrosis or congestive heart failure.

Treatment

The term "treatment," as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e. prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

The Subject/Patient

The subject/patient may be an animal, a mammal or a human.

In the preferred embodiment, the subject/patient is a human.

The ability and potency of the compounds disclosed in the present invention to inhibit aldosterone synthase (CYP11B2) in vitro may be measured by the following assay.

The cell line NCI-H295R (American Type Culture Collection, ATCC, Rockville, Md., USA), originally derived from an adrenal carcinoma and described to secrete aldosterone upon induction of aldosterone synthase (CYP11B2) activity, is cultured in Dulbecco's Modified Eagle'Ham F-12 medium (DME/F12) that is supplemented with Ultroser SF serum (Soprachem, Cergy-Saint-Christophe, France) as well as insulin, transferrin, selenite (I-T-S, Becton Dickinson Biosiences, Franklin Lakes, N.J., USA) and antibiotics in 75 cm$^2$ cell culture flasks at a temperature of 37° C. and a 95% air/5% $CO_2$ humidified atmosphere. The cells are subsequently transferred to a 24-well plate and seeded in the presence of DME/F12 medium that is supplemented with 0.1% bovine serum albumin instead of Ultroser SF serum. The experiment is initiated by incubating the cells for 72 hours in DME/F12 medium supplemented with 0.1% bovine serum albumin and test compounds in the presence of cell stimulatory agents. The test compound is added in a concentration range of 0.2 nanomolar to 20 micromolar. Angiotensin-II (e.g. at 10 or 100 nanomolar concentration), potassium ions (e.g. at 16 millimolar), forskolin (e.g. at 10 micromolar) or a combination of two agents may serve as cell-stimulatory agents. The cellular secretion of aldosterone into the cell culture medium can be quantitatively assessed with commercially available radioimmunoassays and specific antibodies (e.g. Diagnostics Products Corporation, Los Angeles, Calif., USA) according to the manufacturer's instructions. Alternatively, cells may be incubated for a shorter period of time e.g. for 2-8 h, if the Cyp11B2 substrate corticosterone, the immediate pre-cursor of aldosterone biosynthesis, is added to the medium at a concentration of 10 to 100 μM. The external addition of substrate to the incubation medium stabilizes the Cyp11B2 substrate availability and thus circumvents the need to incubate cells for longer than a cell division cycle.

The degree of secretion of a selective steroid is used as a measure of enzyme activity, respectively enzyme inhibition, in the presence or absence of a test compound. The dose-dependent enzyme inhibitory activity of a compound is reflected in an inhibition curve that is characterized by an $IC_{50}$ value (inhibitory concentration in mol/l yielding 50% of the maximal inhibition). The $IC_{50}$ values for active test compounds are generated by simple linear regression analysis to establish inhibition curves without data weighting. The inhibition curve is generated by fitting a 4-parameter logistic function to the raw data of the samples using the least squares approach. The function is described as follows:

$$Y=(d-a)/((1+(x/c)^{-b})+a)$$

with:
a=minimum
b=slope
C=$IC_{50}$
d=maximum
x=inhibitor concentrations

The compounds of the present invention show in the herein described in vitro test systems inhibitory activities with $IC_{50}$ values for aldosterone synthesis inhibition in NCI-H295R ranging from $10^{-4}$ to $10^{-10}$ mol/l.

The target efficacy of the compounds disclosed in the present invention to dose-dependently suppress aldosterone levels in vivo may be assessed with the following protocol:

Adult male Wistar rats weighing between 250 and 350 grams are kept under the usual 12-hour light and 12-hour dark conditions at a temperature of 23° C.±2° C. On the first day of the experiment, the animals receive a subcutaneous injection of a depot ACTH product in a dose of 1.0 mg/kg weight (SYNACTHEN-Depot, Novartis, Basel, CH) 16 hours prior to the administration of a test compound. Pilot studies showed that this ACTH dose significantly increased plasma aldosterone and corticosterone levels by 5- to 20-fold over a period of at least 18 hours. An alternative method to stimulate aldosterone secretion consists in subjecting rats to a low salt diet for 48 hours and applying the diuretic furosemide at 10 mg/kg by subcutaneous or intraperitoneal administration 16 hours, respectively 2 hours prior to the start of the experiment. On the second day of the experiment, the animals are divided into test groups of 5 animals and subjected to a first bleed 1 hour prior to the administration of test compound. Subsequently, and 16 hours after the injection of the ACTH product, the animals receive either vehicle or test compound dissolved in vehicle in a variable dose range from 0.02 to 200 mg/kg by oral gavage. The animals are bled two more times from the vena subclavia under isoflurane anaesthesia 2 and 6 hours after dosing. The blood is collected in heparin-treated tubes. The plasma samples are obtained by centrifugation and stored at −20° C. The blood samples are anti-coagulated with heparin and centrifuged. The aldosterone concentrations of the plasma samples can be determined with a radioimmunoassay as described above for the in vitro test systems. The dose-dependent suppression of plasma aldosterone levels can be evaluated relative to placebo administration or quantitatively using the equation described above for the in vitro test systems to generate ED50 (effective dose in mg/kg yielding 50% of the maximal efficacy) or ED80 values (effective dose in mg/kg yielding 80% of the maximal efficacy).

The compounds of the present invention show in the herein described in vivo protocol relative plasma aldosterone suppression efficacies of −20% to −95% or ED50 values of 0.05-5 mg/kg, respectively, ED80 values of 0.1-10 mg/kg.

The selective suppression of plasma steroid levels as for instance aldosterone in comparison to corticosterone may serve as a measure for in vivo bioavailability and pharmacodynamic enzyme inhibitory activity of the herein described compounds. The evaluation of the data may occur relative to the application of vehicle or quantitatively by determination of the area under the curve (AUC).

Examples of suppression of aldosterone and corticosterone levels:

| Compound of Example | Dose (mg/kg p.o.) | Aldosterone levels (% change[+] at 2 h) | Corticosterone levels (% change[+] at 2 h) |
|---|---|---|---|
| 1 | 4 | −67.6 | −7.7 |
| 4 | 4 | −50.2 | 0.9 |

[+]The resulting changes in plasma aldosterone, respectively corticosterone, levels upon oral administration of a test compound are expressed as percent (%) change that is defined by the ratio of the [(plasma steroid level 2 hours after compound administration) − (plasma steroid level 1 hour prior to compound administration)] divided by (plasma steroid level 1 hour prior to compound administration).

The target selectivity of the herein disclosed compounds particularly in respect to aldosterone synthase related enzymes such as 11beta hydroxylase (CYP11B1) or aromatase (CYP19) can be measured as follows:

The enzyme 11beta hydroxylase (CYP11B1) mediates the rate-limiting step of cortisol biosynthesis in human, respectively, corticosterone biosynthesis in rodent species. As these steroids mediate essential metabolic and stress response functions, compounds intended for the herein disclosed therapeutic use should at therapeutic dose levels show no or only minor interference with 11beta hydroxylase. The dose-dependent interference of the compounds with 11beta hydroxylase can be evaluated by measuring the corticosterone concentrations in the blood samples obtained from the in vivo protocol described above. The corticosterone content can be quantitatively assessed with commercially available radioimmunoassays and specific antibodies (e.g. Diagnostics Products Corporation, Los Angeles, Calif., USA) according to the manufacturer's instructions. The dose-dependent suppression of plasma corticosterone levels can be evaluated relative to placebo administration or quantitatively using the equation described above for the in vitro test systems to generate ED50 (effective dose in mg/kg yielding 50% of the maximal efficacy) values. The relative selectivity of plasma corticosterone suppression over plasma aldosterone suppression can be estimated by division of the ED50 value for corticosterone with the ED50 value for aldosterone.

The compounds of the present invention show in the herein described in vivo protocol relative plasma corticosterone suppression efficacies of 0% to −20% or ED50 values of 5-50 mg/kg.

The enzyme aromatese (CYP19) mediates the rate-limiting step of estrogen biosynthesis in human and rodent species. As estrogens control the sexual characteristics and reproduction as well as various structural and functional tissue features, compounds intended for the herein disclosed therapeutic use should at therapeutic dose levels show no or only minor interference with aromatase.

The concentration-dependent interference of the compounds with aromatase can be measured in vitro using a commercial Cyp19 enzyme inhibition kit and the manufacturer's instructions.

The Cyp19/methoxy-4-trifluoromethyl-coumarin (MFC) high throughput inhibition kit (Becton Dickinson Biosciences, San Jose, Calif., USA), for example, is designed to screen for potential inhibitors of Cyp19 catalytic activity in a 96-well format. The kit includes recombinant human Cyp19 enzyme in the form of supersomes, a fluorescent P450 substrate, an NADPH regenerating system, a reaction buffer and a stop reagent. MFC, the fluorogenic substrate is rapidly converted by Cyp19 supersomes to the highly fluorescent product 7-hydroxy-4-trifluoromethyl coumarin (7-HFC). The execution of the assay in the presence of various concentrations of inhibitor compounds ranging from 0.2 nanomolar to 20 millimolar occurs according to the manufacturer's instructions. The concentration-dependent inhibition of aromatase activity can be quantified using the equation described above for the in vitro testing of aldosterone synthase inhibition in NCI-H295R cells to generate IC50 values (inhibitory concentration in mol/l yielding 50% of the maximal inhibition).

Examples of Aromatase Inhibition:

| Compound of Example | $IC_{50}$ value [nM]* |
|---|---|
| 1 | 64.6 |
| 4 | 406.0 |
| 10 of WO2006/128852 | 11.8 |

*A lower inhibiting activity corresponds to a higher $IC_{50}$ value; average of several measurements. A high $IC_{50}$ value is desired for selectivity reasons.

The pharmacological properties of the herein disclosed compounds are characterized pharmacokinetically by measuring their bioavailability, tissue distribution and elimination as well as metabolically by measuring their interference with drug metabolizing cytochrom P450 enzymes.

The bioavailability of the compounds described herein can be tested in vivo using the following protocol:

A compound is administered intravenously and orally (gavage) in separate sets of pre-catheterized (carotid artery) male rats (300 g±20%). The applied doses for oral administration may range from 0.5 to 50 mg/kg body weight; the doses for intravenous administration may range from 0.5 to 20 mg/kg body weight. Blood samples are collected through the catheter before compound administration and over the subsequent 24-hour period using an automated sampling device (AccuSampler, DiLab Europe, Lund, Sweden). Plasma levels of the compound are determined using a validated LC-MS analytical method. The pharmacokinetic analysis is performed on the plasma concentration-time curves after averaging all plasma concentrations across time points for each route of administration. Typical pharmacokinetics parameters to be calculated include: maximum concentration ($C_{max}$), time to maximum concentration ($t_{max}$), area under the curve from 0 hours to the time point of the last quantifiable concentration ($AUC_{0-t}$), area under the curve from time 0 to infinity ($AUC_{0-inf}$), elimination rate constant (K), terminal half-life ($t_{1/2}$), absolute oral bioavailability or fraction absorbed (F), clearance (CL), and Volume of distribution during the terminal phase (Vd).

The compounds of the present invention show in the herein described in vivo protocol absolute bioavailability values ranging from 40% to 100% and terminal plasma elimination half-times of 2 h to 10 h.

Any interference of the herein disclosed compounds with drug metabolising enzymes can be assessed by measuring inhibitory activities on the five major drug-metabolizing cytochrom P450 enzymes, CYP1A2, CYP2C9, CYP2C19, CYP2D6, and CYP3A4 in vitro using the following methods:

For screening purposes, the inhibitory potential of a test compound can be tested with ready to use kits (CYP450 High Throughput Inhibitor Screening kit, e.g. CYP1A2/CEC, #459500, BD Biosciences, Franklin Lakes, N.J. USA), which are available for all of the five above-mentioned major CYP isoforms. In such kits, recombinant human CYP450 isoforms expressed in insect cells are incubated with isoform specific, fluorogenic substrates in the presence of different test compound concentrations. Enzymatic activity converts the fluorogenic substrate into a fluoro-chrome product, the concentration of which is measured with a fluoro-spectrophotometer. Fluorescence is directly proportional to enzyme activity.

In a typical standard assay using the CYP450 High Throughput Inhibitor Screening kit, a compound is tested at 2 nM to 33 µM concentration range in a phosphate buffer (50 mM, pH 7.4) containing a glucose 6-phosphate dehydrogenase/NADP/NADPH regeneration system and a suitable fluorogenic substrate: e.g. 3-cyano-7-ethoxy-coumarin (CYP1A2). As control inhibitors, the following substances can be used: furafylline (CYP1A2), sulfaphenazole (CYP2C9), tranylcypromine (CYP2C19), quinidine (CYP2D6) and ketoconazole (CYP3A4).

The reaction is started by the addition of 2.5 nM (final concentration) CYP450 isozyme, incubated at 37° C. for 15 to 45 minutes, and then terminated by the addition of 187.5 mM tris-hydroxy-aminomethane base/acetonitrile (20/80, v/v).

The amount of generated fluorochrome is then determined by fluorescence spectroscopy with suitable exitation and emission wavelength settings: e.g. 410 nm excitation and 460 nm emission wavelength (CYP1A2).

Alternatively and/or complimentary, assays using human liver microsomes (e.g. BD Biosciences, #452161) in combination with a CYP isoform-specific standard substrate (e.g. midazolam for CYP3A4/5) as described by R. L. Walsky and R. S. Obach in Validated assay for human cytochrome p450 activities; Pharmacokinetics, Pharmacodynamics, and Drug Metabolism, Pfizer, Groton, Conn.; Drug Metabolism and Disposition: (2004) 32, 647-660, can be used. To determine whether a test compound inhibits CYP3A enzyme activity, for example, hydroxylation of midazolam by human liver microsomes at varying test compound concentrations is monitored. Hydroxy-midazolam production is directly proportional to enzyme activity and can be determined by liquid chromatography-tandem mass spectrometry. Additionally, the microsomal assay can be run without and with a 15 min pre-incubation of microsomes with test compound prior to the addition of standard substrate. Test compounds or their metabolite(s) that have the potential to irreversibly modify the P450 enzyme will have a stronger inhibitory effect after pre-incubation.

In a typical standard assay using the human liver microsome assay, compounds are tested at 10 nM to 50 µM concentration range in a phosphate buffer (100 mM potassium phosphate, 3.3 mM $MgCl_2$, pH 7.4) containing a NADPH regeneration system (glucose 6-phosphate dehydrogenase, NADP, NADPH) and 10 µM substrate (e.g. midazolam for CYP3A4/5) and 0.1 mg/mL microsomal protein. As control inhibitors, the same substances as described above can be used (e.g. ketoconazole (CYP3A4/5)). If pre-incubation of the compound is desired, all assay components except substrate are mixed and incubated for 15 minutes at 37° C. After that period, substrate is added to the assay mix and then incubation at 37° C. is continued for 15 minutes. Without pre-incubation, all assay components are mixed simultaneously and then incubated at 37° C. for 15 minutes. Termination of the enzymatic reaction is achieved by the addition of a $HCOOH/acetonitrile/H_2O$ (Apr. 30, 1966, v/v/v) solution. Samples are then incubated in the refrigerator (4±2° C.) for 1 h±10 min to increase protein precipitation. Directly before analysis by LC/MSMS, the samples are centrifuged at 3,500 g for 60 min at 4° C. to separate precipitated protein. The supernatant is mixed with acetonitrile/water (50/50, v/v), and then directly analyzed for compound content with LC/MSMS.

Evaluation of the data from either experimental setup is then done as follows: the fraction of remaining activity at a specific compound concentration versus the activity in the control as a function of compound concentration is used to compute $IC_{50}$ values. This is done by fitting a 4-parameter logistic function to the experimental data set.

The compounds of the present invention show in the herein described in vitro test systems for drug metabolizing cytochrom P450 enzymes $IC_{50}$ values for CYP2C9 ranging from $10^{-3}$ to $10^{-6}$ mol/l, for CYP2D6 ranging from $10^{-3}$ to $10^{-6}$ mol/l and for CYP3A4 ranging from $10^{-3}$ to $10^{-6}$ mol/l.

In order to achieve the desired effects in a patient to be treated, the compounds of the present invention can be administered orally or enterally, such as, for example, intravenously, intraperitoneally, intramuscularly, rectally, subcutaneously or else by direct injection of the active substance locally into tissues or tumours. The term patient encompasses warm-blooded species and mammals such as, for example, human, primate, bovine, dog, cat, horse, sheep, mouse, rat and pig. The compounds can be administered as a pharmaceutical product or be incorporated into an administration device which ensures sustained release of the compound. The amount of substance to be administered can vary over a wide range and represent every effective dose. Depending on the patient to be treated or the condition to be treated and mode of administration, the dose of the effective substance each day can be between about 0.005 and 50 milligrams per kilogram of body weight, but is preferably between about 0.05 and 5 milligrams per kilogram of body weight each day.

For oral administration, the compounds can be formulated in solid or liquid pharmaceutical forms such as, for example, as capsules, pills, tablets, coated tablets, granules, powders, solutions, suspensions or emulsions. The dose of a solid pharmaceutical form can be one usual hard gelatin capsule which may be filled with active ingredients and excipients such as lubricants and fillers, such as, for example, lactose, sucrose and maize starch. Another form of administration may be represented by tableting of the active substance of the present invention. The tableting can take place with conventional tableting excipients such as, for example, lactose, sucrose, maize starch, combined with binder from gum acacia, maize starch or gelatin, disintegrants such as potato starch or crosslinked polyvinylpyrrolidone (PVPP) and lubricants such as stearic acid or magnesium stearate.

Examples of excipients suitable for soft gelatin capsules are vegetable oils, waxes, fats, semisolid and liquid polyols etc.

Examples of excipients suitable for producing solutions and syrups are water, polyols, sucrose, invert sugar, glucose etc.

For rectal administration, the compounds can be formulated in solid or liquid pharmaceutical forms such as, for example, suppositories. Examples of excipients suitable for suppositories are natural or hardened oils, waxes, fats, semi-liquid or liquid polyols etc.

For parenteral administration, the compounds can be formulated as an injectable dosage of the active ingredient in a liquid or suspension. The preparations usually comprise a physiologically tolerated sterile solvent which may comprise a water-in-oil emulsion, with or without surfactant, and other pharmaceutically acceptable excipients. Oils which can be used for such preparations are paraffins and triglycerides of vegetable, animal or synthetic origin, such as, for example, peanut oil, soya oil and mineral oil. Injectable solutions generally comprise liquid carriers such as, preferably, water, saline, dextrose or related sugar solutions, ethanol and glycols such as propylene glycol or polyethylene glycol.

The substances may be administered as a transdermal patch system, as a depot injection or implant if the formulation makes sustained delivery of the active ingredient possible. The active substance can be compressed as granules or to narrow cylinders and be administered subcutaneously or intramuscularly as a depot injection or implant.

The pharmaceutical products may in addition also comprise preservatives, solubilizers, viscosity-increasing substances, stabilizers, wetting agents, emulsifiers, sweeteners, colorants, aromatizing agents, salts to change the osmotic pressure, buffers, coating agents or antioxidants. They may also comprise other therapeutically valuable substances too.

The compounds of the invention described herein permit the following methods of use:

as therapeutic combination in the form of a product or of a kit which is composed of individual components consisting of a compound described herein, in free form or as pharmaceutically useful salt, and at least one pharmaceutical form whose active ingredient has a blood pressure-lowering, an inotropic, an antidiabetic, an obesity-reducing or a lipid-lowering effect, which can be used either simultaneously or sequentially. The product and the kit may comprise instructions for use.

as method for combined use, such as, for example, in simultaneous or sequential succession, of a therapeutically effective amount of a compound described herein, in free or in pharmaceutically useful salt form, and of a second active ingredient with blood pressure-lowering, inotropic, antidiabetic, obesity-reducing or lipid-lowering effect.

The compounds described herein and their pharmaceutically useful salts can be used in combination with (i) one or more blood pressure-lowering active ingredients, as such for example:

renin inhibitors such as aliskiren, SPP635, SPP676, MK8141;
angiotensin II receptor blockers such as candesartan, irbesartan, olmesartan, losartan, valsartan, telmisartan etc.;
ACE inhibitors such as quinapril, ramipril, trandolapril, lisinopril, captopril, enalapril etc.;
calcium antagonists such as nifedipine, nicardipine, verapamil, isradipine, nimodipine, amlodipine, felodipine, nisoldipine, diltiazem, fendiline, flunarizine, perhexyline, gallopamil etc.;
diuretics such as hydrochlorothiazide, chlorothiazide, acetazolamide, amiloride, bumetanide, benzthiazide, etacrynic acid, furosemide, indacrinone, metolazone, triamterene, chlorthalidone, etc.;
aldosterone receptor blockers such as spironolactone, eplerenone, canrenoate;
endothelin receptor blockers such as bosentan, darusentan, ambrisentan, sitaxentan;
phosphodiesterase inhibitors such as aminone, sildenafil;
direct vasodilators such as dihydralazine, minoxidil, pinacidil, diazoxide, nitroprusside, flosequinan etc.;
α- and β-receptor blockers such as phentolamine, phenoxybenzamine, prazosin, doxazosin, terazosin, carvedilol, atenolol, metoprolol, nadolol, propranolol, timolol, carteolol etc.;
neutral endopeptidase (NEP) inhibitors such as candoxatril, sinorphan, SCH34826 and SCH42495;
sympatholytics such as methyldopa, clonidine, guanabenz, reserpine (ii) one or more agents having inotropic activity, as such for example:

cardiac glycosides such as digoxin;
β-receptor stimulators such as dobutamine;
thyroid hormone such as thyroxine (iii) one or more agents having antidiabetic activity, as such for example:

insulins such as insulin aspart, insulin human, insulin lispro, insulin glargine and further fast-, medium- and long-acting insulin derivatives and combinations
insulin sensitizers such as rosiglitazone, pioglitazone;
sulfonylureas such as glimepiride, chlorpropamide, glipizide, glyburide etc.;
biguanides such as metformin;
glucosidase inhibitors such as acarbose, miglitol, voglibose;
meglitinides such as repaglinide, nateglinide, mitiglinide;
Dipeptidyl peptidase IV inhibitors such as sitagliptin, vildagliptin, alogliptin, denagliptin, saxagliptin etc.
GLP-1 analogues such as exenatide, liraglutide, albugutide (iv) one or more obesity-reducing ingredients, as such for example:

lipase inhibitors such as orlistat;
appetite suppressants such as sibutramine, phentermine;

(v) one or more lipid-lowering ingredients, such as, for example,

HMG-CoA reductase inhibitors such as lovastatin, fluvastatin, pravastatin, atorvastatin, simvastatin, rosuvastatin etc.;
fibrate derivatives such as fenofibrate, gemfibrozil etc.;
bile acid-binding active ingredients such as colestipol, colestyramine, colesevelam;
cholesterol absorption inhibitors such as ezetimibe;
nicotinic acid such as niacin and other agents which are suitable for the treatment of high blood pressure, heart failure or vascular disorders associated with diabetes and renal disorders, such as acute or chronic renal failure, in humans and animals. Such combinations can be used separately or in products which comprise a plurality of components.

The compounds described herein and their pharmaceutically acceptable salts can additionally be used in combination with (i) a diagnostic test system which permits quantitative determination of the plasma aldosterone level (PAC, plasma aldosterone concentration)
(ii) a diagnostic test system which permits quantitative determination of the plasma renin level (PRC, plasma renin concentration)
(iii) a diagnostic test system which permits quantitative determination of the plasma renin activity (PRA, plasma renin activity)
(iv) a diagnostic test system which permits quantitative determination of the plasma aldosterone/renin level (ARC, aldosterone renin concentration)
(v) a diagnostic test system which permits quantitative determination of the plasma aldosterone/renin activity (ARR, aldosterone to renin activity ratio)
(vi) a diagnostic test system which permits quantitative determination of the plasma cortisol level (PCC, plasma cortisol concentration)

Such diagnosis-therapy combinations can be used separately or in products which comprise a plurality of components.

EXAMPLES

The following examples illustrate the present invention. All temperatures are stated in ° C. Celsius, pressures in mbar. Unless mentioned otherwise, the reactions take place at room temperature. The abbreviation "Rf=xx(A)" means for example that the Rf is found in solvent system A to have the value xx. The proportion of solvents to one another is always stated in fractions by volume. Chemical names of end products and intermediates were generated with the aid of the AutoNom 2000 (Automatic Nomenclature) program. Chemical names of spiro-compounds were generated with the aid of the ACD/Name V11.0 program from ACD/Labs.

HPLC-Gradients on Hypersil BDS C-18 (5 μm); column: 4×125 mm:
Gradient I: 90% water/10% acetonitrile* to 0% water/100% acetonitrile* in 5 minutes+2.5 minutes (1.5 ml/min)
Gradient II: 99% water*/1% acetonitrile* to 0% water/100% acetonitrile* in 10 minutes+2 minutes (1.5 ml/min)
Gradient III: 99% water*/1% acetonitrile* to 0% water/100% acetonitrile* in 10 minutes+2 minutes (1.0 ml/min)
HPLC-Gradients on Synergi 4 μm POLAR-RP 80A; column: 4.60×100 m:
Gradient III: 90% water/10% acetonitrile* to 0% water/100% acetonitrile* in 5 minutes+2.5 minutes (1.5 ml/min)
* contains 0.1% trifluoroacetic acid
The abbreviations used are as follows:

| Rf | ratio of distance travelled by a substance to distance of the eluent from the starting point in thin-layer chromatography |
|---|---|
| Rt | retention time of a substance in HPLC (in minutes) |
| m.p. | melting point (temperature) |

Example 1

6',7'-Dihydro-3H,5'H-spiro[2-benzofuran-1,8'-imidazo[1,5-a]pyridine]-5-carbonitrile A mixture of 1.93 mmol of 5-bromo-6',7'-dihydro-3H,5'H-spiro[2-benzofuran-1,8'-imidazo[1,5-a]pyridine] and 9.63 mmol of copper(I) cyanide in 10 ml of N-methyl-pyrrolidone is heated to 150° C. for 72 h. The reaction mixture is cooled to room temperature and poured into a mixture of 25% aqueous ammonia and ethyl acetate. The mixture is stirred vigorously for 15 minutes and the layers are separated. The aqueous layer is extracted with ethyl acetate and the combined organics are washed with water, dried over sodium sulfate, filtered and concentrated under reduced pressure. The resulting residue is purified by flash chromatography (SiO$_2$ 60 F) followed by crystallization from diethyl ether to afford the title compound as a beige solid. Rf=0.15 (dichloromethane-2M ammonia in ethanol 97:3); Rt=4.66 (gradient II).

The starting materials are prepared as follows:

a) 5-Bromo-6',7'-dihydro-3H,5'H-spiro[2-benzofuran-1,8'-imidazo[1,5-a]pyridine]

A solution of 0.43 mmol of 8-(4-bromo-2-hydroxymethyl-phenyl)-5,6,7,8-tertrahydro-imidazo[1,5-a]pyridin-8-ol in 2.8 ml of 1N aqueous HCl is heated to 100° C. for 1.5 h. The solution is cooled to room temperature and poured into saturated aqueous sodium bicarbonate solution. The mixture is extracted with ethyl acetate-tert-butyl-methyl ether. The combined organics are dried over sodium sulfate, filtered and concentrated under reduced pressure. The title compound is obtained as brown oil and used for the next step without further purification. Rf=0.15 (toluene-methanol 85:15); Rt=5.69 (gradient II).

b) 8-(4-Bromo-2-hydroxymethyl-phenyl)-5,6,7,8-tetrahydro-imidazo[1,5-a]pyridin-8-ol A solution of 6.55 mmol of (5-bromo-2-iodo-benzyloxy)-tert-butyl-dimethyl-silane in 20 ml of tetrahydrofuran is cooled to −20° C. 6.55 mmol of an isopropymagnesium chloride solution (2M in tetrahydrofuran) is added dropwise and stirring continued for 1 h at −20° C. A solution of 4.37 mmol of 6,7-dihydro-5H-imidazo[1,5-a]pyridin-8-one [426219-51-4] in 40 ml of tetrahydrofuran is added dropwise and the reaction mixture stirred for 40 minutes at −20° C. The reaction mixture is poured into a mixture of 0.1N aqueous HCl and dichloromethane and the layers are separated. The aqueous layer is basified with sodium bicarbonate and extracted with ethyl acetate. The combined organic layers are dried over sodium sulfate, filtered and concentrated under reduced pressure. The title compound is obtained as a white foam and used for the next step without further purification. Rt=4.61 (gradient II).

c) (5-Bromo-2-iodo-benzyloxy)-tert-butyl-dimethyl-silane

A solution of 9.59 mmol (5-bromo-2-iodo-phenyl)-methanol [199786-58-8] in 10 ml of N,N-dimethylformamide is added at room temperature dropwise to a mixture of 11.5 mmol of sodium hydride (60% in paraffine) in 20 ml of N,N-dimethylformamide. The mixture is stirred for 1 h at room temperature. 10.6 mmol of tert-butyl-dimethylchloro silane and 1.00 mmol of potassium iodide are added and the mixture stirred for 30 minutes at room temperature. The reaction is quenched with water and extracted with toluene. The combined organics are washed with brine, dried over sodium sulfate, filtered and concentrated under reduced pressure. The resulting residue is purified by flash chromatography (SiO$_2$ 60 F) to afford the title compound as colourless oil. Rf=0.35 (dichloromethane); Rt=11.31 (gradient II).

Example 2

5',6'-Dihydro-3H-spiro[2-benzofuran-1,7'-pyrrolo[1,2-c]imidazole]-5-carbonitrile To a degassed solution of 31.2 mmol of 5-bromo-5',6'-dihydro-3H-spiro[2-benzofuran-1,7'-pyrrolo[1,2-c]imidazole]] in 90 ml of N,N-dimethylformamide are added 62.4 mmol of zinc(II) cyanide and 1.25 mmol of [1,1'-bis(diphenylphosphino)ferrocene]-dichloro palladium. The mixture is heated at 120° C. for 16 h. The mixture is poured into ice water and extracted with ethyl acetate. The combined organics are dried over magnesium sulfate, filtered and concentrated under reduced pressure. The resulting residue is purified by flash chromatography (SiO$_2$ 60 F) followed by crystallization from diethyl ether to afford the title compound as a beige solid. Rf=0.33 (dichloromethane-2M ammonia in ethanol 95:5); Rt=4.62 (gradient II).

The starting material is prepared as follows:

a) 5-Bromo-5',6'-dihydro-3H-spiro[2-benzofuran-1,7'-pyrrolo[1,2-c]imidazole]]

The title compound is obtained according to the procedure described in examples 1a and 1b starting from 5,6-dihydro-5H-pyrrolo[1,2-c]imidazol-7-one [426219-43-4] and (5-bromo-2-iodo-benzyloxy)-tert-butyl-dimethyl-silane (example 1c). White foam; Rt=4.62 (gradient II).

Example 3

3-Oxo-5',6'-dihydro-3H-spiro[2-benzofuran-1,7'-pyrrolo[1,2-c]imidazole]-5-carbonitrile The title compound is prepared according to the procedure described for example 2 starting from 5-bromo-5',6'-dihydro-3H-spiro[2-benzofuran-1,7'-pyrrolo[1,2-c]imidazol]-3-one. White foam; Rf=0.07 (dichloromethane-2M ammonia in ethanol 96:4); Rt=3.79 (gradient II).

The starting material is prepared as follows:

a) 5-Bromo-5',6'-dihydro-3H-spiro[2-benzofuran-1,7'-pyrrolo[1,2-c]imidazol]-3-one To a solution of 2.27 mmol of spiro[(5'-bromo-1',3'-dihydro-isobenzofuran)-1',7-(6,7-dihydro-5H-pyrrolo[1,2-c]imidazole)] (example 2a) in 50 ml of dichloromethane is added a finely powdered mixture of 3.0 g of manganese(IV) dioxide and 1.0 g of potassium permanganate. The reaction mixture is stirred for 60 h at room temperature and filtered over Hyflo. The filtrate is concentrated under reduced pressure. The resulting residue is purified by flash chromatography (SiO$_2$ 60 F) to afford the title compound as white foam. Rf=0.25 (dichloromethane-2M ammonia in Ethanol 97:3); Rt=4.90 (gradient II).

Example 4

6',7'-Dihydro-3H,5'H-spiro[2-benzofuran-1,8'-imidazo[1,5-a]pyridine]-6-carbonitrile A 22 ml Supelco vial under Argon is loaded with 0.231 mmol of tris(dibenzylidene-acetone)dipalladium(0) (Pd$_2$(dba)$_3$) and 0.463 mmol of 1,1'-bis(diphenyl-phosphino)ferrocene (dppf). 5 ml of dry N,N-dimethyl acetamide is added and the dark solution is stirred at room temperature for 10 minutes. 1.388 mmol of zinc cyanide, and then a solution of 2.313 mmol of 6-chloro-6',7'-dihydro-3H,5'H-spiro[2-benzofuran-1,8'-imidazo[1,5-a]pyridine] in 2.5 ml of dry N,N-dimethyl acetamide are successively added. The reaction mixture is briefly degassed, put under an atmosphere of Argon then directly placed in an oil bath pre-heated to 80° C. The dark brown mixture is then stirred for 15 hours at 140° C. If the conversion is not complete (HPLC check), a fresh solution of Pd$_2$(dba)$_3$ and dppf in N,N-dimethyl acetamide, previously stirred at room temperature for 10 minutes, is added and the stirring is continued at 140° C. till no more starting material is detected. The reaction mixture is cooled to room temperature and evaporated to dryness. The residue is diluted with 30 ml of dichloromethane and 100 ml of tert-butyl-methyl ether and washed with aqueous HCl 2N (2×50 ml). The combined aqueous phases are basified with 75 ml of 4N aqueous NaOH and extracted with dichloromethane (3×200 ml). The combined organic phases are dried over sodium sulfate, filtered and concentrated under reduced pressure. The resulting residue is purified by flash chromatography (SiO$_2$ 60 F) to afford the title compound as a beige solid. Rf=0.13 (EtOAc-methanol 10:1); Rt=2.59 (gradient I).

The starting materials are prepared as follows:

a) 6-Chloro-6',7'-dihydro-3H,5'H-spiro[2-benzofuran-1,8'-imidazo[1,5-a]pyridine]

A suspension of 2.672 mmol of 8-[2-(tert-butyl-dimethyl-silanyloxymethyl)-5-chloro-phenyl]-5,6,7,8-tetrahydro-imidazo[1,5-a]pyridin-8-ol in 40 ml of 1N aqueous HCl is stirred at 95° C. for 40 hours, then cooled to room temperature. The mixture is basified to pH 12 by dropwise addition of aqueous saturated sodium bicarbonate solution, and then extracted with dichloromethane (3×140 ml). The combined organic phases are dried over sodium sulfate, filtered and concentrated under reduced pressure. The resulting residue is purified by flash chromatography (SiO$_2$ 60 F) to afford the title compound as a beige solid. Rf=0.14 (EtOAc-methanol 10:1); Rt=3.04 (gradient I).

b) 8-[2-(tert-Butyl-dimethyl-silanyloxymethyl)-5-chloro-phenyl]-5,6,7,8-tetrahydro-imidazo[1,5-a]pyridin-8-ol A solution of 7.272 mmol of tert-butyllithium (1.7 M in pentane) is added dropwise to a solution of 7.272 mmol of tert-butyl-(4-chloro-2-iodo-benzyloxy)-dimethyl-silane in 27 ml of dry diethyl ether at −78° C. under argon atmosphere. The turbid solution is stirred at −78° C. for 1 minute, then a solution of 3.636 mmol of 6,7-dihydro-5H-imidazo[1,5-a]pyridin-8-one [426219-51-4] in 12 ml of dry tetrahydrofuran is added dropwise. After 5 minutes of stirring at −78° C., the reaction is quenched with the addition of 20 ml of aqueous saturated sodium bicarbonate-solution and 20 ml of water. 80 ml of dichloromethane is then added and the mixture is warmed to room temperature. The organic phase is separated and the aqueous phase is extracted with dichloromethane (2×80 ml). The combined organic phases are dried over sodium sulfate, filtered and evaporated. The residue is purified by flash chromatography (SiO$_2$ 60 F) to afford the title product as a white solid. Rf=0.14 (EtOAc-methanol=10:1); Rt=4.74 (gradient I).

c) tert-Butyl-(4-chloro-2-iodo-benzyloxy)-dimethyl-silane

The title compound is obtained according to the procedure described for example 1c starting from (4-chloro-2-iodo-phenyl)-methanol [244104-55-0]. Colourless oil. Rf=0.78 (EtOAc-heptane=1:19); Rt=7.17 (gradient I).

The following compounds 5 to 22 are prepared in a manner analogous to the processes described in Example 4.

Example 5

3',4',6,7-Tetrahydro-5H-spiro[imidazo[1,5-a]pyridine-8,1'-isochromene]-7'-carbonitrile using 2-(4-chloro-2-iodo-phenyl)-ethanol instead of (4-chloro-2-iodo-phenyl)-methanol [244104-55-0] in step c. Beige solid. Rf=0.11 (EtOAc-methanol 10:1); Rt=2.84 (gradient I).

The starting materials are prepared as follows:

a) 2-(4-Chloro-2-iodo-phenyl)-ethanol

A solution of 52.73 mmol of borane tetrahydrofuran complex (1N in tetrahydrofuran) is added dropwise to a stirred solution of 21.09 mmol of (4-chloro-2-iodo-phenyl)-acetic acid in 150 ml of dry tetrahydrofuran. The reaction mixture is stirred at room temperature for 1 hour then 20 ml of methanol are carefully added. The mixture is refluxed at 60° C. for 45 minutes, and then evaporated to dryness. The resulting residue is purified by flash chromatography ($SiO_2$ 60 F) to afford the title product as a yellowish solid. Rf=0.13 (EtOAc-heptane=1:4); Rt=4.27 (gradient I).

b) (4-Chloro-2-iodo-phenyl)-acetic acid

A mixture of 16.05 mmol of (4-chloro-2-iodo-phenyl)-acetonitrile [882689-31-8] in 50 ml of tetrahydrofuran, 50 ml of ethanol and 50 ml of 2N aqueous NaOH is stirred at 80° C. for 45 hours then the organic solvents are evaporated. The remaining aqueous phase is acidified with 4N aqueous HCl and extracted with ethyl acetate (3×100 ml). The combined organic phases are dried over sodium sulfate, filtered and concentrated under reduced pressure. The title compound is obtained as a white solid and used for the next step without further purification. Rt=4.06 (gradient I).

Example 6

3',4',6,7-Tetrahydro-5H-spiro[imidazo[1,5-a]pyridine-8,1'-isochromene]-6'-carbonitrile using from 2-(5-bromo-2-iodo-phenyl)-ethanol instead of (4-chloro-2-iodo-phenyl)-methanol [244104-55-0] in step c. Beige solid. Rf=0.12 (EtOAc-methanol 10:1); Rt=2.81 (gradient I).

The starting material is prepared as follows:

a) 2-(5-Bromo-2-iodo-phenyl)-ethanol

The title compound is obtained according to the procedure described for example 5a starting from (5-bromo-2-iodo-phenyl)-acetic acid [702641-01-8]. Yellowish crystals. Rf=0.22 (EtOAc-heptane=1:4); Rt=4.31 (gradient I).

Example 7

5',6'-Dihydro-3H-spiro[2-benzofuran-1,7'-pyrrolo[1,2-c]imidazole]-6-carbonitrile using from (4-chloro-2-iodo-phenyl)-methanol [244104-55-0] instead of (4-chloro-2-iodo-phenyl)-methanol [244104-55-0] in step c and 5,6-dihydro-5H-pyrrolo[1,2-c]imidazol-7-one [426219-43-4] instead of 6,7-dihydro-5H-imidazo[1,5-a]pyridin-8-one [426219-51-4] in step b. Beige solid. Rf=0.11 (EtOAc-methanol 10:1); Rt=2.41 (gradient I).

Example 8

3,4,5',6'-Tetrahydrospiro[isochromene-1,7'-pyrrolo[1,2-c]imidazole]-6-carbonitrile using from 2-(5-bromo-2-iodo-phenyl)-ethanol (example 6a) instead of (4-chloro-2-iodo-phenyl)-methanol [244104-55-0] in step c and 5,6-dihydro-5H-pyrrolo[1,2-c]imidazol-7-one [426219-43-4] instead of 6,7-dihydro-5H-imidazo[1,5-a]pyridin-8-one [426219-51-4] in step b. Beige solid, Rf=0.14 ($CH_2Cl_2$—$NH_3$ (2M in ethanol) 95:5); Rt=4.93 (gradient III).

Example 9

3,4,5',6'-Tetrahydrospiro[isochromene-1,7'-pyrrolo[1,2-c]imidazole]-7-carbonitrile using from 2-(4-chloro-2-iodo-phenyl)-ethanol (example 5a) instead of (4-chloro-2-iodo-phenyl)-methanol [244104-55-0] in step c and 5,6-dihydro-5H-pyrrolo[1,2-c]imidazol-7-one [426219-43-4] instead of 6,7-dihydro-5H-imidazo[1,5-a]pyridin-8-one [426219-51-4] in step b. Braun solid, Rf=0.20 ($CH_2Cl_2$—$NH_3$ (2M in ethanol) 95:5); Rt=4.96 (gradient III).

Example 10

7'-Fluoro-3',4',6,7-tetrahydro-5H-spiro[imidazo[1,5-a]pyridine-8,1'-isochromene]-6'-carbonitrile using from 2-(2-bromo-5-chloro-4-fluoro-phenyl)-ethanol (example 5a) instead of (4-chloro-2-iodo-phenyl)-methanol [244104-55-0] in step c.

The starting materials are prepared as follows:

a) 2-(2-Bromo-5-chloro-4-fluoro-phenyl)-ethanol

The title compound is obtained according to the procedure described for example 5a starting from (2-bromo-5-chloro-4-fluoro-phenyl)-acetic acid and is identified based on the Rf value.

b) (2-Bromo-5-chloro-4-fluoro-phenyl)-acetic acid

The title compound is obtained according to the procedure described for example 5b starting from (2-bromo-5-chloro-4-fluoro-phenyl)acetonitrile and is identified based on the Rf value.

c) (2-Bromo-5-chloro-4-fluoro-phenyl)-acetonitrile

A mixture of 1 mmol of 1-bromo-2-bromomethyl-4-chloro-5-fluoro-benzene and 4 mmol of sodium cyanide in 3 ml of dry N,N-dimethylformamide is stirred at room temperature till complete conversion is observed. The reaction mixture is quenched by the addition of water and the mixture is extracted with tert-butyl-methyl ether. The combined organic phases are washed with brine, dried over sodium sulfate, filtered and concentrated under reduced pressure. The resulting residue is purified by flash chromatography ($SiO_2$ 60 F) to afford the title compound which is identified based on the Rf value.

d) 1-Bromo-2-bromomethyl-4-chloro-5-fluoro-benzene

A solution of 75 mmol of 1-bromo-4-chloro-5-fluoro-2-methyl-benzene, 75 mmol of 1-bromo-pyrrolidine-2,5-dione and 0.74 mmol of benzoyl peroxide in 100 ml of carbon tetrachloride is heated to reflux for 15 hours. After evaporation of the solvent, the residue is partitioned between water and ethyl acetate. The organic layer is washed with water, and then with brine, dried over sodium sulfate, filtered and concentrated under reduced pressure. The resulting residue is purified by flash chromatography ($SiO_2$ 60 F) to afford the title compound which is identified based on the Rf value.

e) 1-Bromo-4-chloro-5-fluoro-2-methyl-benzene 1.25 mol of 5-bromo-2-chloro-4-methyl-phenylamine are added to 750 ml of concentrated aqueous HCl and the mixture is stirred at 80° C. until formation of a homogenous suspension, then the mixture is cooled to 0° C. and a solution of 1.38 mmol of sodium nitrite in 330 ml of water is added dropwise over 1 hour. The mixture is stirred for an additional 20 minutes and then a solution of 700 ml of fluoroboric acid (prepared by dissolving 264 g of boric acid in 744 ml of 40% aqueous hydrofluoric acid) is added. After 30 minutes of stirring, the separated fluoroborate is filtered off, washed successively with small amounts of fluoroboric acid solution, ethanol and water, and dried in vacuo. Thermal decomposition of the fluoroborate is carried out in a flask at 130-170° C. The distillate is partitioned between water and diethyl ether. The organic phase is washed successively with 10% aqueous NaOH, 3N aqueous HCl and water, dried over sodium sulfate, filtered and concentrated under reduced pressure. The resulting residue is purified by flash chromatography ($SiO_2$ 60 F) to afford the title compound which is identified based on the Rf value.

f) 5-Bromo-2-chloro-4-methyl-phenylamine

In an autoclave, a mixture of 253 mmol of 1-bromo-4-chloro-2-methyl-5-nitro-benzene [10289-13-1], 2 g of Raney nickel (60% aqueous) and 1.5 g of formamidine acetate in 102 ml of methanol is stirred under an atmosphere of hydrogen (pressure 12 bars) at 80° C. for 1 hour. The mixture is cooled to room temperature, filtered and evaporated. The residue is partitioned between aqueous saturated sodium bicarbonate-solution and tert-butyl-methyl ether. The aqueous phase is extracted with tert-butyl-methyl ether. The combined organic phases are dried over sodium sulfate, filtered and concentrated under reduced pressure. The resulting residue is purified by flash chromatography ($SiO_2$ 60 F) to afford the title compound which is identified based on the Rf value.

Example 11

6-Fluoro-6',7'-dihydro-3H,5'H-spiro[2-benzofuran-1,8'-imidazo[1,5-a]pyridine]-5-carbonitrile using from (2-bromo-5-chloro-4-fluoro-phenyl)-methanol instead of (4-chloro-2-iodo-phenyl)-methanol [244104-55-0] in step c.

The starting material is prepared as follows:

a) (2-Bromo-5-chloro-4-fluoro-phenyl)-methanol

A solution of 227 mmol of 1-bromo-2-bromomethyl-4-chloro-5-fluoro-benzene (example 10d) in 300 ml of glacial acetic acid containing 495 mmol of potassium acetate is heated to reflux for 3 hours. The mixture is concentrated and then partitioned between water and diethyl ether. After repeated extractions with diethyl ether, the combined organic layers are washed successively with saturated sodium bicarbonate-solution solution and water, dried over magnesium sulfate and concentrated. The crude acetate is dissolved in 200 ml of methanol and treated slowly with a methanolic KOH solution (33.4 g in 100 ml). The reaction mixture is stirred for 35 minutes at room temperature, then neutralized with acetic acid and concentrated under reduced pressure. The residue is partitioned between water and diethyl ether. Concentration of the organic phase affords the crude title compound which is purified by flash chromatography ($SiO_2$ 60 F) to afford the title compound which is identified based on the Rf value.

Example 12

5',6'-Dihydro-3H-spiro[2-benzofuran-1,7'-pyrrolo[1,2-c]imidazole]-5,6-dicarbonitrile using from (2-bromo-4,5-dichloro-phenyl)-methanol instead of (4-chloro-2-iodo-phenyl)-methanol [244104-55-0] in step c and 5,6-dihydro-5H-pyrrolo[1,2-c]imidazol-7-one [426219-43-4].

The starting material is prepared as follows:

a) (2-Bromo-4,5-dichloro-phenyl)-methanol

The title compound is obtained according to the procedure described for example 5a starting from 2-bromo-4,5-dichloro-benzoic acid [93361-95-6] and is identified based on the Rf value.

Example 13

6-Fluoro-5',6'-dihydro-3H-spiro[2-benzofuran-1,7'-pyrrolo[1,2-c]imidazole]-5-carbonitrile using from (2-bromo-5-chloro-4-fluoro-phenyl)-methanol (example 11a) instead of (4-chloro-2-iodo-phenyl)-methanol [244104-55-0] in step c and 5,6-dihydro-5H-pyrrolo[1,2-c]imidazol-7-one [426219-43-4] instead of 6,7-dihydro-5H-imidazo[1,5-a]pyridin-8-one [426219-51-4] in step b.

Example 14

7-Fluoro-3,4,5',6'-tetrahydrospiro[isochromene-1,7'-pyrrolo[1,2-c]imidazole]-6-carbonitrile using from 2-(2-bromo-5-chloro-4-fluoro-phenyl)-ethanol (example 10a) instead of (4-chloro-2-iodo-phenyl)-methanol [244104-55-0] in step c and 5,6-dihydro-5H-pyrrolo[1,2-c]imidazol-7-one [426219-43-4] instead of 6,7-dihydro-5H-imidazo[1,5-a]pyridin-8-one [426219-51-4] in step b.

Example 15

6-Fluoro-3,4,5',6'-tetrahydrospiro[isochromene-1,7'-pyrrolo[1,2-c]imidazole]-7-carbonitrile using from 2-(2-bromo-4-chloro-5-fluoro-phenyl)-ethanol instead of (4-chloro-2-iodo-phenyl)-methanol [244104-55-

0] in step c and 5,6-dihydro-5H-pyrrolo[1,2-c]imidazol-7-one [426219-43-4] instead of 6,7-dihydro-5H-imidazo[1,5-a]pyridin-8-one [426219-51-4] in step b.

The starting materials are prepared as follows:

a) 2-(2-Bromo-4-chloro-5-fluoro-phenyl)-ethanol

The title compound is obtained according to the procedure described for example 5a starting from (2-bromo-4-chloro-5-fluoro-phenyl)-acetic acid and is identified based on the Rf value.

b) (2-Bromo-4-chloro-5-fluoro-phenyl)-acetic acid

The title compound is obtained according to the procedure described for example 5b starting from 2-bromo-4-chloro-5-fluoro-phenyl)-acetonitrile and is identified based on the Rf value.

c) (2-Bromo-4-chloro-5-fluoro-phenyl)-acetonitrile

The title compound is obtained according to the procedure described for example 10c starting from 1-bromo-2-bromomethyl-5-chloro-4-fluoro-benzene and is identified based on the Rf value.

d) 1-Bromo-2-bromomethyl-5-chloro-4-fluoro-benzene 0.55 mmol of phosphorous tribromid is added dropwise to a solution of 1 mmol of (2-Bromo-4-chloro-5-fluoro-phenyl)-methanol in 40 ml of dichloromethane. The trouble reaction solution is stirred at room temperature for 2 hours, diluted with 100 ml of diethylether and decanted. The supernatant is washed with 10 ml of 2N sodium bicarbonate solution, 20 ml of water and 20 ml of brine, dried over sodium sulfate, filtered and concentrated under reduced pressure at 28° C. to afford the title compound which is identified based on the Rf value.

e) (2-Bromo-4-chloro-5-fluoro-phenyl)-methanol

The title compound is obtained according to the procedure described for example 5a starting from 2-bromo-4-chloro-5-fluoro-benzaldehyde and is identified based on the Rf value.

f) 2-Bromo-4-chloro-5-fluoro-benzaldehyde

A solution of 1 mmol of n-butyllithium (1N in hexane) is added dropwise to a solution of 1 mmol of 1-bromo-5-chloro-4-fluoro-2-iodo-benzene in 20 ml of tetrahydrofuran cooled to −78° C. After the addition, 1.1 mmol of N,N-dimethylformamide is added and the mixture is allowed to warm to room temperature. 100 ml of tert-butylmethyl ether then 20 ml of water are added. The organic phase is separated, washed with 20 ml of brine, dried over sodium sulfate, filtered and concentrated under reduced pressure. The resulting residue is purified by flash chromatography ($SiO_2$ 60 F) to afford the title compound which is identified based on the Rf value.

g) 1-Bromo-5-chloro-4-fluoro-2-iodo-benzene 99 mmol of 2-bromo-4-chloro-5-fluoro-phenylamine [120694-11-3] is dissolved in 700 ml of water and 100 ml of concentrated sulfuric acid. The solution is cooled to 0° C. and 109 mmol of sodium nitrite dissolved in 30 ml of water is added. The mixture is stirred for 1 hour at 5-10° C. then a solution of 130 mmol of potassium iodide in 100 ml of water is added slowly whilst the mixture is vigorously stirred. After addition, the mixture is allowed to warm to room temperature. Ethylacetate is added and the phases are separated. The aqueous phase is extracted with ethyl acetate (3×). The combined organic phases are washed successively with 1N NaOH, 1N sodium thiosulfate, 1N HCl, aq.sat. sodium bicarbonate solution and brine, then dried over sodium sulfate, filtered and concentrated under reduced pressure. The resulting residue is purified by flash chromatography ($SiO_2$ 60 F) to afford the title compound which is identified based on the Rf value.

Example 16

5-Fluoro-5',6'-dihydro-3H-spiro[2-benzofuran-1,7'-pyrrolo[1,2-c]imidazole]-6-carbonitrile using from (2-bromo-4-chloro-5-fluoro-phenyl)-methanol (example 15e) instead of (4-chloro-2-iodo-phenyl)-methanol [244104-55-0] in step c and 5,6-dihydro-5H-pyrrolo[1,2-c]imidazol-7-one [426219-43-4] instead of 6,7-dihydro-5H-imidazo[1,5-a]pyridin-8-one [426219-51-4] in step b.

Example 17

6-Fluoro-3',4',6,7-tetrahydro-5H-spiro[imidazo[1,5-a]pyridine-8,1'-isochromene]-7'-carbonitrile using from 2-(2-bromo-4-chloro-5-fluoro-phenyl)-ethanol (example 15a) instead of (4-chloro-2-iodo-phenyl)-methanol [244104-55-0] in step c.

Example 18

5-Fluoro-6',7'-dihydro-3H,5'H-spiro[2-benzofuran-1,8'-imidazo[1,5-a]pyridine]-6-carbonitrile using from (2-bromo-4-chloro-5-fluoro-phenyl)-methanol (example 15e) instead of (4-chloro-2-iodo-phenyl)-methanol [244104-55-0] in step c.

Example 19

5,6-Difluoro-5',6'-dihydro-3H-spiro[2-benzofuran-1,7'-pyrrolo[1,2-c]imidazole]

using from (2-bromo-4,5-difluoro-phenyl)-methanol [476620-55-0] instead of (4-chloro-2-iodo-phenyl)-methanol [244104-55-0] in step c and 5,6-dihydro-5H-pyrrolo[1,2-c]imidazol-7-one [426219-43-4] instead of 6,7-dihydro-5H-imidazo[1,5-a]pyridin-8-one [426219-51-4] in step b.

Example 20

6',7'-Difluoro-3',4',6,7-tetrahydro-5H-spiro[imidazo[1,5-a]pyridine-8,1'-isochromene]

using from 2-(2-bromo-4,5-difluoro-phenyl)-ethanol instead of (4-chloro-2-iodo-phenyl)-methanol [244104-55-0] in step c.

The starting materials are prepared as follows:

a) 2-(2-Bromo-4,5-difluoro-phenyl)-ethanol

The title compound is obtained according to the procedure described for example 5a starting from (2-bromo-4,5-difluoro-phenyl)-acetic acid and is identified based on the Rf value.

b) (2-Bromo-4,5-difluoro-phenyl)-acetic acid

The title compound is obtained according to the procedure described for example 5b starting from (2-bromo-4,5-difluoro-phenyl)-acetonitrile and is identified based on the Rf value.

c) (2-Bromo-4,5-difluoro-phenyl)-acetonitrile

The title compound is obtained according to the procedure described for example 10c starting from 1-bromo-2-bromomethyl-4,5-difluoro-benzene [647862-95-1] and is identified based on the Rf value.

Example 21

5,6-Difluoro-6',7'-dihydro-3H,5'H-spiro[2-benzofuran-1,8'-imidazo[1,5-a]pyridine]

using from (2-bromo-4,5-difluoro-phenyl)-methanol [476620-55-0] instead of (4-chloro-2-iodo-phenyl)-methanol [244104-55-0] in step c.

Example 22

6,7-Difluoro-3,4,5',6'-tetrahydrospiro[isochromene-1,7'-pyrrolo[1,2-c]imidazole]

using from 2-(2-bromo-4,5-difluoro-phenyl)-ethanol (example 20a) instead of (4-chloro-2-iodo-phenyl)-methanol [244104-55-0] in step c and 5,6-dihydro-5H-pyrrolo[1,2-c]imidazol-7-one [426219-43-4] instead of 6,7-dihydro-5H-imidazo[1,5-a]pyridin-8-one [426219-51-4] in step b.

Example 23

(1S) or (1R)-5',6'-Dihydro-3H-spiro[2-benzofuran-1,7'-pyrrolo[1,2-c]imidazole]-5-carbonitrile The racemic compound 5',6'-dihydro-3H-spiro[2-benzofuran-1,7'-pyrrolo[1,2-c]imidazole]-5-carbonitrile (Example 2) is fractionated into the enantiomers by chiral preparative HPLC*. The title compound is isolated as the enantiomer which elutes second. Rt **=17.21 min.

* HPLC Method (Preparative):
Column: 250×30 mm CHIRALPAK® AD 20 μm
Mobile phase: $CO_2$/methanol 80:20
Flow rate: 240 ml/min
Detection: UV 230 nm
Temperature: 25° C.
Pressure: 150 bar
** HPLC Method (Analytical):
Column: 250×4.6 mm CHIRALPAK® AD-H 5 μm
Mobile phase: n-heptane/ethanol/ethylenediamine 60:40:0.1
Flow rate: 1 ml/min
Detection: DAD 240 nm
Temperature: 25° C.

The invention claimed is:

1. A compound of formula (I)

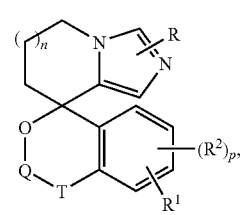

in which

Q is —$C(R^3)(R^4)$— or a bond;

T is —$C(R^3)(R^4)$—;

R is hydrogen or deuterium;

$R^1$ is $C_1$-$C_8$-alkyl, $C_0$-$C_8$-alkylcarbonyl, amino, mono- or di-$C_1$-$C_8$-alkylamino, $C_0$-$C_8$-alkyl-carbonylamino, $C_0$-$C_8$-alkylcarbonyl-$C_1$-$C_8$-alkylamino, carbamoyl, mono- or di-$C_1$-$C_8$-alkylaminocarbonyl, carboxyl, carboxy-$C_1$-$C_4$-alkyl, halogen, cyano, methylsulfonyl, nitro, trifluoro-methyl, $C_1$-$C_8$-alkoxy, $C_1$-$C_8$-alkoxycarbonyl, heterocyclyl or aryl, which radicals may be unsubstituted or substituted by 1-4 $C_1$-$C_8$-alkyl, $C_0$-$C_8$-alkylcarbonyl, halogen, cyano, oxo, trifluoromethyl, trifluoromethoxy, $C_0$-$C_8$-alkylcarbonylamino, $C_0$-$C_8$-alkylcarbonyl-$C_1$-$C_8$-alkylamino, carbamoyl, mono- and di-$C_1$-$C_8$-alkylaminocarbonyl, carboxy-$C_0$-$C_4$-alkyl, $C_1$-$C_8$-alkoxy, $C_1$-$C_8$-alkoxycarbonyl, aryl or heterocyclyl;

$R^2$ is, if p is not 0, independently of one another, $C_1$-$C_8$-alkyl, $C_0$-$C_8$-alkylcarbonyl, amino, mono- and di-$C_1$-$C_8$-alkylamino, $C_0$-$C_8$-alkylcarbonylamino, $C_0$-$C_8$-alkylcarbonyl-$C_1$-$C_8$-alkyl-amino, carbamoyl, mono- or di-$C_1$-$C_8$-alkylaminocarbonyl, carboxyl, carboxy-$C_1$-$C_4$-alkyl, halogen, cyano, methylsulfonyl, nitro, trifluoromethyl, trifluoromethoxy, $C_1$-$C_8$-alkoxy, $C_1$-$C_8$-alkoxycarbonyl, heterocyclyl or aryl, which radicals may be unsubstituted or substituted by 1-4 $C_1$-$C_8$-alkyl, $C_0$-$C_8$alkylcarbonyl, halogen, cyano, oxo, trifluoromethyl, trifluoromethoxy, $C_0$-$C_8$-alkylcarbonylamino, $C_0$-$C_8$-alkylcarbonyl-$C_1$-$C_8$-alkylamino, carbamoyl, mono- and di-$C_1$-$C_8$-alkylaminocarbonyl, carboxy-$C_0$-$C_4$-alkyl, $C_1$-$C_8$-alkoxy, $C_1$-$C_8$-alkoxycarbonyl, aryl or hetero-cyclyl;

$R^3$ is, independently of one another:

a) hydrogen or $C_1$-$C_8$-alkyl; or b) together with $R^4$ oxo;

$R^4$ is, independently of one another:

a) hydrogen or $C_1$-$C_8$-alkyl; or b) together with $R^3$ oxo;

n is a number 0, 1 or 2;

p is a number 0, 1 or 2;

or its pharmaceutically useful salt.

2. The compound according to claim 1, wherein it conforms to formula (I')

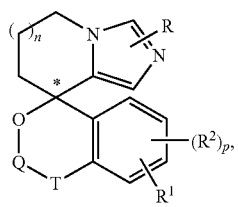 (I')

wherein the definitions of the substituents R, $R^1$, $R^2$, Q, T, n and p are as defined according to the compounds of the formula (I) according to claim 1, having a specific configuration at the asymmetric carbon atom labelled "*", and which compound shows an aromatase inhibitory activity at least 10 times lower than the compound of the formula (I') with the opposite configuration around the asymmetric carbon atom labelled "*".

3. The compound according to claim 1, wherein $R^1$ is $C_1$-$C_8$-alkyl, $C_0$-$C_8$-alkylcarbonyl, halogen, cyano, methylsulfonyl, nitro, trifluoromethyl, trifluoromethoxy, $C_0$-$C_8$-alkylcarbonylamino, $C_0$-$C_8$-alkylcarbonyl-$C_1$-$C_8$-alkylamino, carbamoyl, mono- and di-$C_1$-$C_8$-alkylaminocarbonyl, carboxy-$C_0$-$C_4$-alkyl, $C_1$-$C_8$-alkoxy, $C_1$-$C_8$-alkoxycarbonyl or heterocyclyl.

4. The compound according to claim 1, wherein $R^2$ is, if p is not 0, independently of one another, halogen, cyano, methylsulfonyl, nitro, trifluoromethyl, trifluoromethoxy, or $C_1$-$C_8$-alkyl.

5. The compound according to claim 1, wherein n is a number 0 or 1.

6. The compound according to claim 1, wherein
$R^1$ is acetyl, halogen, cyano, methylsulfonyl or nitro; and
$R^2$ is, if p is not 0, independently of one another, halogen, cyano, methylsulfonyl, nitro or $C_1$-$C_8$-alkyl.

7. The compound according to claim 1, wherein
$R^1$ is cyano or halogen;
$R^2$ is, if p is not 0, cyano or halogen;
n is a number 0 or 1; and
p is a number 0 or 1.

8. A pharmaceutical composition comprising a compound of the formula (I) or a pharmaceutically useful salt thereof, according to claim 1, and a conventional excipient.

9. A pharmaceutical combination in the form of a product or kit composed of individual components consisting of a) a compound of the formula (I) or a pharmaceutically useful salt thereof, according to claim 1, and b) at least one pharmaceutical form whose active ingredient has a blood pressure-lowering, an inotropic, an antidiabetic, an obesity reducing or a lipid-lowering effect.

10. The compound according to claim 2, having a specific configuration at the asymmetric carbon atom labelled "*", which compound shows an aromatase inhibitory activity at least 20 times lower than the compound of the formula (I') with the opposite configuration around the asymmetric carbon atom labelled "*".

11. The compound according to claim 3, wherein $R^1$ is acetyl, halogen, cyano, methylsulfonyl or nitro.

12. The compound according to claim 4, wherein $R^2$ is, if p is not 0, independently of one another, halogen, cyano, methylsulfonyl, nitro or $C_1$-$C_8$-alkyl.

13. The compound according to claim 7, wherein $R^1$ is cyano or fluoro.

* * * * *